United States Patent
Dinkelborg et al.

(10) Patent No.: US 6,709,693 B1
(45) Date of Patent: Mar. 23, 2004

(54) STENTS WITH A RADIOACTIVE SURFACE COATING, PROCESSES FOR THEIR PRODUCTION AND THEIR USE FOR RESTENOSIS PROPHYLAXIS

(75) Inventors: Ludger Dinkelborg, Berlin (DE); Friedhelm Blume, Berlin (DE); Christoph-Stephan Hilger, Berlin (DE); Dieter Heldmann, Berlin (DE); Johannes Platzek, Berlin (DE); Ulrich Niedballa, Berlin (DE); Heribert Miklautz, Berlin (DE); Ulrich Speck, Berlin (DE); Stephan Duda, Tuebingen (DE); Gunnar Tepe, Wankheim (DE); Bernhard Noll, Freital (DE); Heidemarie Goerner, Dresden (DE)

(73) Assignee: Schering Aktiengesellschaft, Berlin (DE)

( * ) Notice: Subject to any disclaimer, the term of this patent is extended or adjusted under 35 U.S.C. 154(b) by 184 days.

(21) Appl. No.: 09/627,321

(22) Filed: Jul. 27, 2000

Related U.S. Application Data (63) Continuation of application No. 09/403,924, filed as application No. PCT/EP98/02527 on Apr. 29, 1998, now abandoned.

(30) Foreign Application Priority Data

| Apr. 30, 1997 | (DE) | 197 18 340 |
| Apr. 30, 1997 | (DE) | 197 18 341 |
| Apr. 30, 1997 | (DE) | 197 18 342 |
| Jun. 3, 1997 | (DE) | 197 24 223 |
| Jun. 3, 1997 | (DE) | 197 24 229 |
| Jun. 3, 1997 | (DE) | 197 24 230 |

(51) Int. Cl.$^7$ .................. A61L 27/00; B05D 1/18
(52) U.S. Cl. .............. 427/2.24; 427/2.28; 427/2.3; 427/407.1; 427/409; 427/414; 427/417; 427/418; 427/435
(58) Field of Search ............. 427/2.24, 2.28, 427/2.3, 2.1, 407.1, 409, 414, 417, 418, 435

(56) References Cited

U.S. PATENT DOCUMENTS

| 5,059,166 | A |   | 10/1991 | Fischell et al. |
| 5,176,617 | A |   | 1/1993 | Fischell et al. |
| 5,213,561 | A |   | 5/1993 | Weinstein et al. |
| 5,722,984 | A | * | 3/1998 | Fischell et al. ............ 600/3 |
| 5,851,315 | A | * | 12/1998 | Strathearn et al. ........ 148/239 |
| 5,919,126 | A | * | 7/1999 | Armini ..................... 600/3 |
| 6,103,295 | A |   | 8/2000 | Chan et al. |
| 6,152,869 | A | * | 11/2000 | Park et al. ................ 600/3 |
| 6,261,320 | B1 | * | 7/2001 | Tam et al. ............... 623/1.15 |
| 6,287,249 | B1 | * | 9/2001 | Tam et al. ................ 600/3 |

* cited by examiner

Primary Examiner—Shrive P. Beck
Assistant Examiner—Jennifer Kolb Michener
(74) Attorney, Agent, or Firm—Millen, White, Zelano & Branigan, P.C.

(57) ABSTRACT

The invention relates to radioactive stents, characterized in that the stent is coated on the surface with the radioactive isotope, as well as processes for their production.

10 Claims, 3 Drawing Sheets

Galvanization Cell

Figure 1:
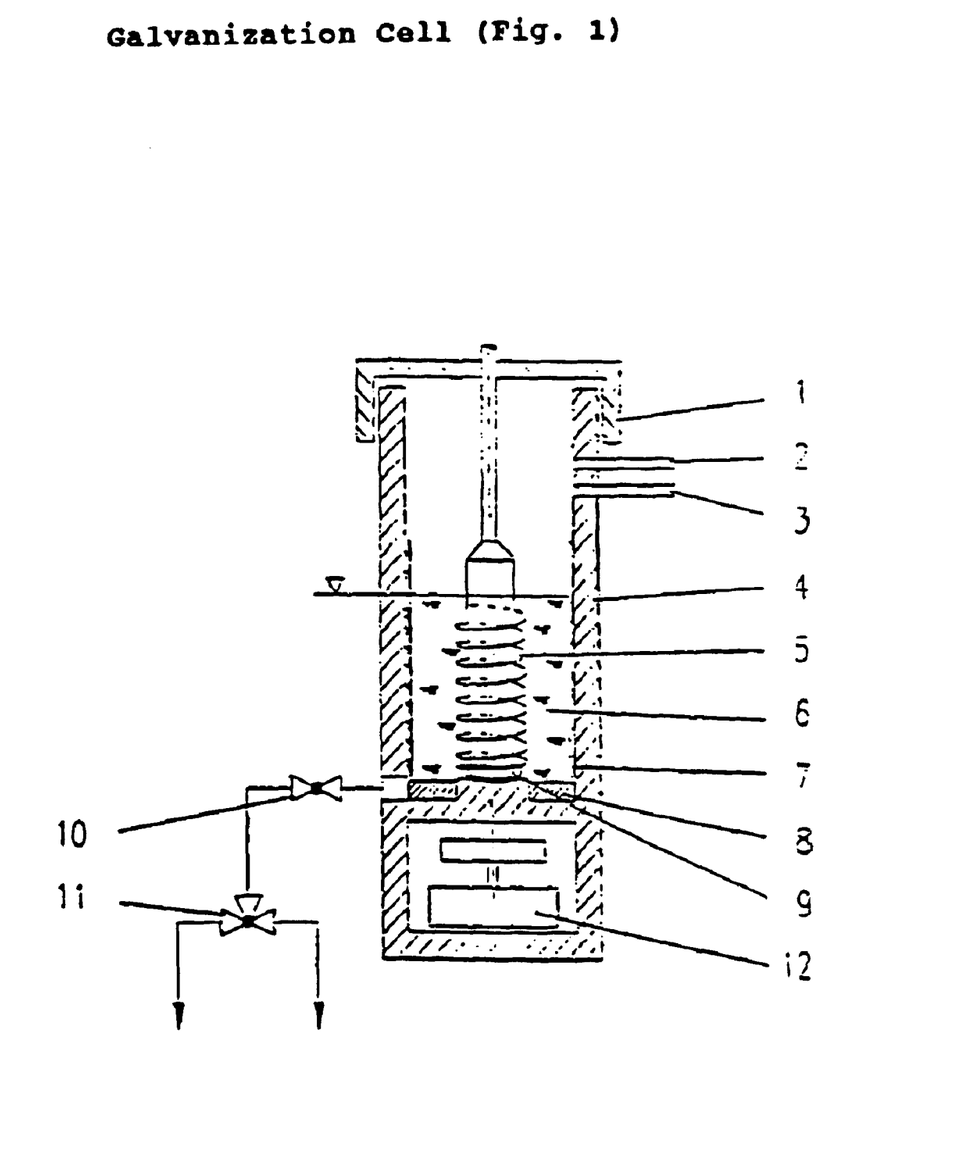

Galvanization Cell (Fig. 1)

Figure 2A:
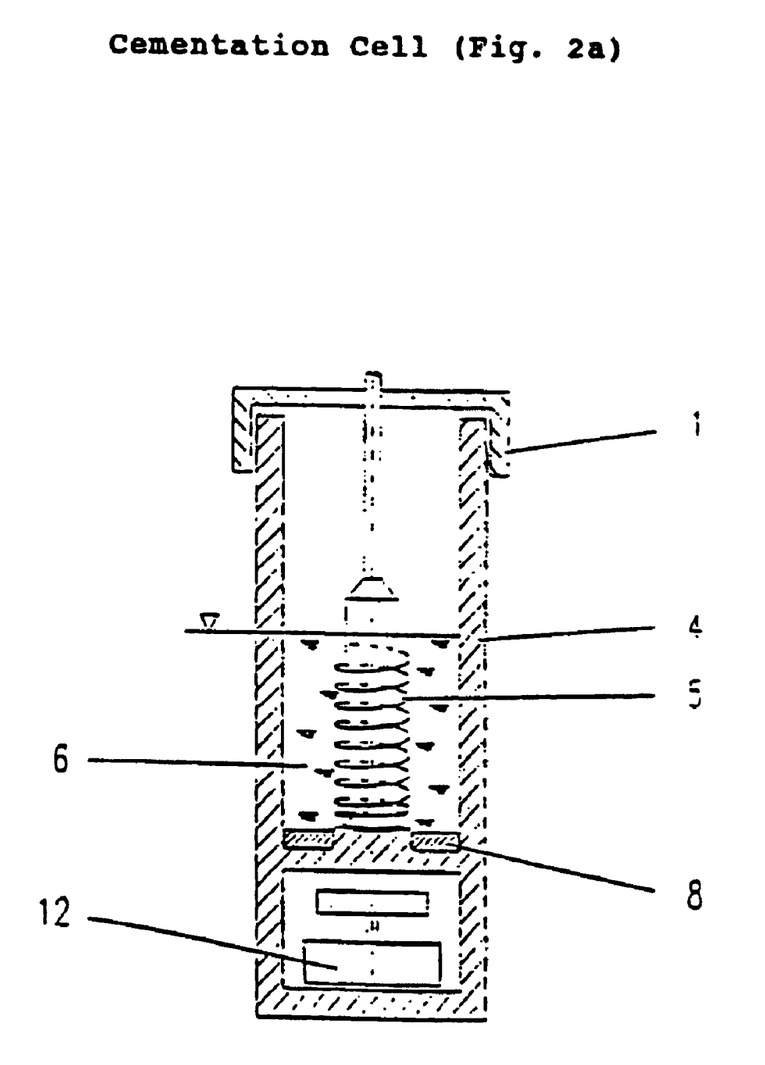

Cementation Cell (Fig. 2a)

Figure 2B:
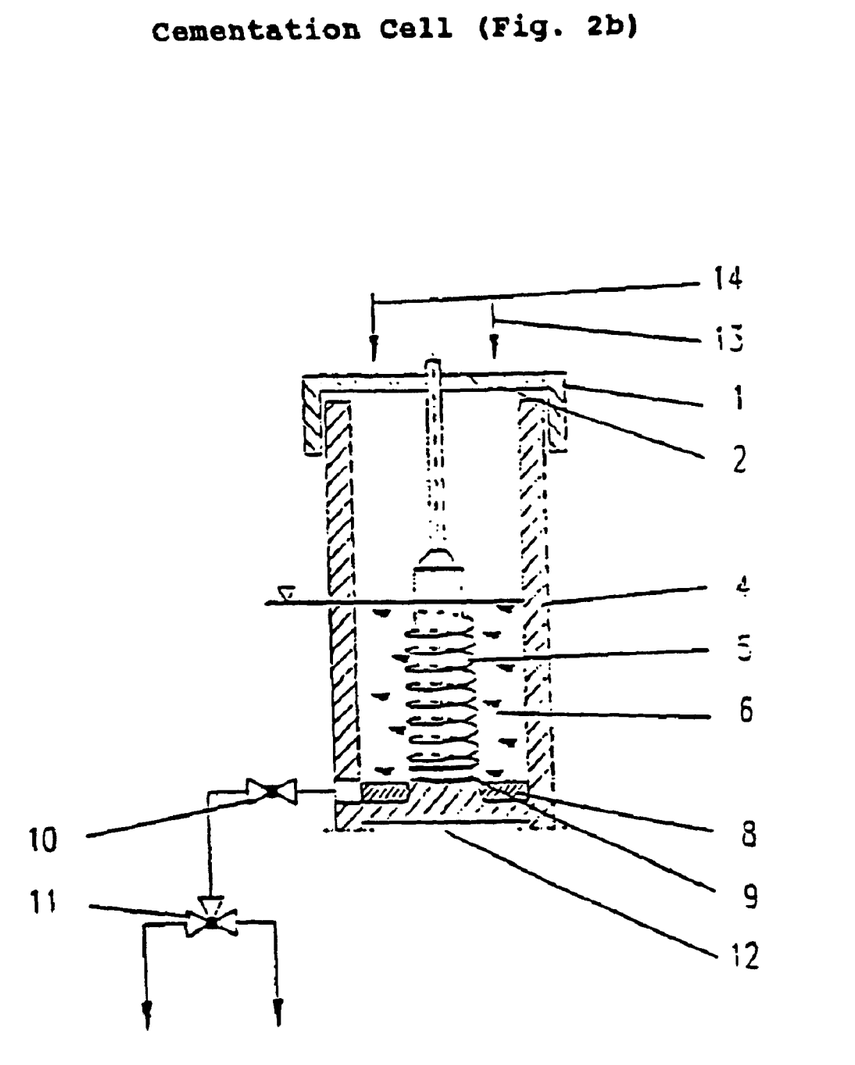

Cementation Cell (Fig. 2b)

STENTS WITH A RADIOACTIVE SURFACE COATING, PROCESSES FOR THEIR PRODUCTION AND THEIR USE FOR RESTENOSIS PROPHYLAXIS

This application is a Continuation of application Ser. No. 09/403,924 Filed on Apr. 29, 1998 as PCT/EP98/02527 designating the U.S.

The invention relates to stents with a radioactive surface coating, processes for their production and their use for restenosis prophylaxis.

PRIOR ART

Radioactive stents are prior art (EP 0433011, WO 94/26205, U.S. Pat. No. 5,176,617). Stents are endoprostheses that make it possible to keep open duct-like structures in the bodies of humans or animals (e.g., vascular, esophageal, tracheal and bile duct stents). They are used as palliative measures in the case of stenoses by obstruction (e.g., arteriosclerosis) or external pressure (e.g., in the case of tumors). Radioactive stents are used, for example, after vascular-surgery interventions or radiological interventions (e.g., balloon angioplasty) for restenosis prophylaxis. Such radioactive stents can be produced, for example, by activation of a non-radioactive stent using irradiation with protons or deuterons from a cyclotron (WO 94/26205). This process for the production of radioactive stents is named ion implantation.

There is now the problem that, on the one hand, generally no cyclotron is available at the site of the use of the stent to undertake an activation of the stent, and, on the other hand, the activated stent cannot be stored indefinitely or transported in any arbitrary way due to the sometimes short half-life of the activated isotope and for reasons of protection against radiation.

The object of this invention is therefore to make available stents and new processes for their production, and said stents can be activated independently by a cyclotron. In particular, the object of the invention is to make available stents that can be coated independently by a cyclotron with a preselected radioactive isotope.

This object is achieved by the stents that are described below and the processes for their production, as they are characterized in the claims.

DESCRIPTION OF THE INVENTION

The above-described object is achieved by the production processes for radioactive stents that are described below. In contrast to ion implantation, the processes according to the invention for the production of radioactive stents are based on chemical or electrochemical methods.

Within the framework of this application, the notations $^{nn}$X and X-nn (X: element symbol, nn: mass number) are to be regarded as synonymous for radioactive isotopes (Example: $^{110}$Ag corresponds to Ag-110).

The above-described object is achieved in a first variant by a process for the production of a radioactive stent, in which a chemical deposition of the radioactive isotope is carried out on the stent.

To this end, the selected stent is immersed in a solution that contains the radioactive isotope. The radioactive isotope is then chemically deposited on the stent. Depending on the selected material of the stent, on the one hand, and the radioactive isotope that is to be deposited, on the other hand, two possible types of deposition are considered:

1) Chemical Reduction

During chemical reduction, a reducing agent (e.g., $SnCl_2$, $KBH_4$, dimethylborane, formaldehyde, sodium hypophosphite) is added to the solution that contains the radioactive isotope in dissolved form as well as the stent.

Survey:

Reducing agent hypophospbite (with Ni)

Addition of citrate, acetate, fluoride, succinate, lactate, propionate pH=4–11

Reducing agent $NaBH_4$ (with Au, Ni)

Additions of dimethylammonium borane, boric acid, citric acid, malonic acid, glycine, pyrophosphate, malic acid, pH=4–10

Reducing agent formaldehyde: (with Cu)

with the addition of NaKtartrate, NaOH

Reducing agent hydrazine: (with Pd, Pt)

Pd, Pt with the addition of $NH_4OH$, EDTA,

Reducing agent dimethylaminoborane $(CH_3)_2NH$—$BH_3$ (with Au, Ag)

Au and Ag from cyanidic baths

After 1 minute to 10 hours, the stent is removed from the respective solution and washed. The stent is coated on the surface with the radioactive isotope.

In this way, for example, radioisotopes of elements Ag, Au, Bi, Co, Cr, Cu, Fe, Gd, Hg, Ho, In, Ir, Lu, Mn, Ni, P, Pb, Pd, Pm, Pt, Re, Rh, Ru, Sc, Sm, Tb, Tc or Y can be deposited on metal stents (e.g., steel, nitinol).

2) Chemical Precipitation

During chemical precipitation, a precipitating agent (e.g., oxalic acid, phosphoric acid or salts thereof or $Na_2CO_3$) is added to the solution that contains the radioactive isotope in dissolved form as well as the stent.

In this way, for example, radioisotopes of elements Ag, Au, Bi, Co, Cr, Cu, Fe, Gd, Hg, Ho, In, Ir, Lu, Mn, Ni, Pb, Pd, Pm, Pt, Re, Rh, Ru, Sc, Sm, Tb, Tc or Y can be deposited on metal stents (e.g., steel, nitinol).

The above-described object is achieved in a second variant, in that the radioactive isotope is secured by means of an adhesive to the surface of the stent.

The device according to the invention thus consists of the metal parent substance of the stent, an adhesive on the surface of the stent and an adhesive radioactive isotope.

As a parent substance, the commercially available vascular implants can be used, e.g., a Wiktor stent, a Strecker stent or a Palmaz-Schatz stent.

As adhesives, peptides, fats or gold in combination with a thiol-group-containing complexing agent are used.

It is thus possible, for example, to use modified polyurethanes that in turn contain complexing agents.

As adhesives, however, peptides can also be used that on the one hand carry a complexing agent and on the other hand bind specifically to the metal of the stent. Examples of these compounds ar labeled endothelin derivatives, as they are described in, e.g., EP 606683, DE 4425778, DE 43 37 600, DE 4337599 and DE 19652374 (e.g., Tc-99m-Asp-Gly-Gly-Cys-Gly-Cys-Phe-(Dr-Trp)-Leu-Asp-Ile-Ile-Trp).

As adhesives, fats that carry a complexing agent can also b used. Examples of this are the complexing agents that carry lipophilic radicals and that are mentioned in DE 43 40 809, EP 450742, EP 438206, EP 413405 or WO 96/26182.

Moreover, gold in combination with a thiol-group-containing complexing agent can also be used as an adhesive. It is known that thiol-group-containing compounds show an increased affinity to gold-coated surfaces (H. Schönherr et al. J. Am. Chem. Soc. 118 (1996), 13051–13057). Surprisingly enough, elementary gold that is on the surface of the stent is also able to secure specific complexing agents, if they have thiol groups. The complexing agents in turn secure the radioactive isotopes.

For the purposes of this document, complexing agents are, e.g., DTPA, DOTA, DO3A, EDTA, TTHA, $MAG_2$-amides, $MAG_3$-amides and derivatives thereof.

As radioactive isotopes, the radioactive isotopes of elements Ag, Au, Ba, Bi, C, Co, Cr, Cu, Fe, Gd, Hg, Ho, In, Ir, Lu, Mn, Ni, P, Pb, Pd, Pm, Pt, Re, Rh, Ru, S, Sb, Sc, Sm, Tb, Tc or Y can be used.

The invention therefore relates to radioactive stents, characterized in that the radioactive isotope is secured to the surface of the stent by means of an adhesive.

The stents according to the invention can be produced as follows by way of example:

A. Peptide as an adhesive

A.1 First, a peptide is selected that for its part is able to complex heavy metal ions. The latter is activated by reaction with the radioactive isotope (e.g., $^{186}$Re or $^{188}$Re) optionally together with a reducing agent. The radiolabled peptide is dissolved in a solvent (e.g., water, phosphate buffer), and the stent is immersed in the peptide solution. After the stent is removed from the peptide solution, it is dried in a drying chamber at room temperature. After the stent is washed, the latter is ready for use.

A.2 In a variant of the process, the uncoated stent is first coated with the non-activated peptide. The thus coated stent is then immersed in a solution that contains the radioactive metal (e.g., $^{186}$Re or $^{188}$Re) optionally together with a reducing agent (e.g., $SnCl_2$) and thus is charged with this isotope. After the stent is washed, the latter is ready for use.

B. Fat as an adhesive

B.1 An uncoated stent is first coated with a lipophilic compound (e.g., 3,9-bis(carboxymethyl)-6-bis (octadecyl)-aminocarbonylmethyl-3,6,9-triazaundecanedioic acid, WO 96/26182) as an adhesive. This lipophilic compound carries a DTPA radical as a complexing agent. The stent can be directly immersed in the compound or a solution thereof. After the stent is coated with the compound, it is mixed with a solution of the radioactive metal (e.g. $^{90}YCl_3$). After the stent is washed, the latter is ready for use.

B.2 In a variant of this process, the coating of the stent is carried out in two stages. In this regard, the stent is first treated with a lipophilic compound that carries amino groups. The amino groups are then reacted with DTPA-monoanhydride, as it is described in the literature. The stent now has a coating that carries the complexing agents (here: DTPA). The stent that is coated in this way is then mixed with a solution of radioactive metal (e.g. $^{90}YCl_3$). After the stent is washed, the latter is ready for use.

C. Gold/thiol-group-containing complexing agents as adhesives

C.1 An uncoated stent is first coated electrochemically with elementary gold (by internal electrolysis, cementation). The gold-coated stent is then immersed in an aqueous solution of a thiol-group-containing complexing agent (e.g., N,N-dimethyl-2-(3,3,5,11,13, 13-hexamethyl-1,2-dithia-5,8,11-triazacyclotridecan-8-yl)-ethylamine or the coupling product of 11-amino-undecyl-1-thiol with DTPA-bis-anhydride). The thiol-group-containing complexing agent adheres to the gold-coated stent. The stent that is prepared in such a way is now mixed with a solution of the radioactive metal (e.g., $^{67}CuSO_4$). After the stent is washed, the latter is ready for use.

The complexing agent can be synthesized on the surface of the stent. It is possible to apply first only one component of the complexing agent to the gold-coated stent and then to couple this component with additional partial units. This procedure is described in detail in the examples.

C.2 In a variant of this process, the gold-coated stent is mixed with a solution of the thiol-group-containing complexing agent, which for its part already complexes a radioactive isotope. After the stent is washed, the latter is ready for use.

C.3 In a variant of this process, the gold-coated stent is mixed with a solution of the thiol-group-containing compound, which in turn contains $^{35}$S. After the stent is washed, the latter is ready for use.

C.4 In another variant of this process, the gold-coated stent is mixed with a solution of the thiol-group-containing complexing agent, whereby the thiol group is labeled with $^{35}$S, and the complexing agent already complexes a radioactive isotope (e.g., $^{67}$Cu). After the stent is washed, the latter is ready for use.

The above-described processes are generally performed at temperatures of 0–100° C. In the coating of the stent with the adhesive, solvents can be used on the basis of the respective adhesive. When a non-aqueous solvent is used, the latter is to be removed before the implantation.

The stents can also be coated with two or more different isotopes. It is possible in particular to apply short-lived or long-lived isotopes together on a stent (for example, $^{55}$Co with $^{55}$Fe, $^{35}$S with $^{67}$Cu or $^{99}$Mo with $^{57}$Co).

The operations that are necessary for implementing the above process that is described in principle are known to one skilled in the art. Special embodiments are described in detail in the examples.

In a third variant, the invention also relates to a process for the production of radioactive stents, which is characterized in that a non-radioactive stent is immersed in a solution that contains at least one radioactive isotope in ionic form, and the isotope is then chemically deposited on the stent.

The above-described object is achieved according to the invention by an electrochemical deposition of the radioactive metal isotope on the stent.

To this end, the selected stent is immersed in a solution that contains the radioactive metal isotope. The radioactive isotope is then electrochemically deposited. On the basis of the selected materials of the stent, on the one hand, and the radioactive isotope that is to be deposited, on the other hand, two possible types of deposition are considered:

I) Electroplating (external electrolysis)

During electroplating, the dissolved radioactive isotope is deposited reductively by applying electrical direct current to the stent that is connected as a cathode.

In this way, for example, copper, technetium, rhenium, silver or indium can be deposited on electrically conducting stents (e.g., steel, nitinol).

II) Cementation (internal electrolysis)

During cementation, the dissolved noble radioactive isotope is deposited on the non-noble stent material without applying electrical current due to the position of the materials in the voltage sequence of the metals. In this way, for example, gold, silver or copper can be deposited on metal stents (e.g., steel, nitinol).

DETAILED DESCRIPTION OF THE INVENTION

For the coating of metal stents, two electrochemical processes have proven especially suitable: electroplating (electrolytic coating) and cementation (internal electrolysis). The process with the broader range of application is the electroplating, since it also makes possible the coating with an electrochemically more negative material than that of the stent. The coating also makes possible chemical reactions—for example reductive processes.

From the user-friendly operation, it can be seen that the cementation is the better process: the stent is added to the solution of an electrochemically more positive element, and the coating is carried out without a parasitic current.

By suitable cell shape, the excess coating material can be kept small. The necessary stirring can be done by a magnetic stirrer or by moving the stent manually. Since only small amounts of substance are applied in this process, manual stirring is reasonable. The same also holds true for reactions at elevated temperature: because of the short time available, thermostating is not necessary; preheating is all that is required.

The coating of cells (FIGS. 1, 2) can be carried out with hypodermic syringes or—in the case of larger stents—with the aid of metering pumps. With these larger cells, it is useful to separate used electrolyte solution (active) and washing liquid (inactive) to keep the volume of active liquid small.

In the cells that are described in FIGS. 1, 2, the stent is placed with its carrier in the vessel, whereby an elevated location with a trough provides for the positioning. In the case of a galvanization cell, this trough contains a Pt sheet as a contact for the stent that is connected as a cathode. A Pt network is located on the cell wall as an anode. By using on of the ring-shaped sheets which is connected in an electrically conducting manner with the anode and that is made of another metal, the operation can also be done with tin, zinc or copper anodes.

The use of the stent with its carrier has the advantage that the inside of the stent is shielded, and thus no coating is carried out there. The coating is carried out only at the locations that are directed against the vessel.

Since a restenosis is suppressed by the coating, an electropolishing of the crude stent may be omitted—especially in the case of high-grade steel.

Possible Types of Electrochemical Labeling of Stents: Galvanostatic Deposition

For this purpose, a battery (1.5–12 V) that is connected with a variable resistor and 2 electrode terminals is sufficient. The metal that is to be coated is connected as a cathode. As an anode, a noble metal, preferably platinum, should be used. The electrolysis period is 20 seconds to 30 minutes. The operation is performed at temperatures of 0°–80° C., but preferably at room temperature.

Cu: (e.g., Cu-67, $\beta$ and $\gamma$ Str., $t_{1/2}$=61.9 h)

from pyrophosphate baths of the composition below:

| | |
|---|---|
| $Cu^{2+}$ | 20–40 g |
| $(P_2O_7)^{4-}$ | 15–250 g |
| $NO_3-$ | 5–10 g |
| $NH_3$ | 1–3 g |
| $(HPO_4)^{2-}$ | <110 g |
| pH | 8–9 |
| I | 1–8 A/dm$^2$ | from alkaline CuCN baths at pH 12.2–12.8 from acid baths of
  sulfate-oxalate-boric acid
  Cucl/Na-thiosulfate
  fluoroborate, fluorosilicate, formate
  $Cu^{11}$/gluconate, lactate, maleate, tartrate I=1–2.5 A/dm$^2$

U=0.2–6 V pH=1.2

Au: (Au-199, $t_{1/2}$=3, $\beta$ and $\gamma$ Str.)

from cyanidic baths with the addition of phosphate and citrate at pH 5–12, from baths of $NH_4ClKAuCN_2$ with the addition of thiourea at pH 6.5–7

I=0.1–0.6 A/dm$^2$

In:

from cyanidic baths at pH=0–1 from fluoroborate baths with the addition of tartaric acid at pH 1

$In_2(SO_4)_3$ pH 2–3/or sulfamate and tartrate

Re: from perrhenate Re-186 citrate+$H_2SO_4$, pH 1–5

I=1–15 A/dm$^2$

Ni:

from $NiSO_4$/boric acid or from acetate, fluoroborate or sulfamate baths, pH=1–5

I=2–30 A/dm$^2$

Pt, Rh, Pd, Ru:

(Pt-197, $t_{1/2}$=$\beta$ Str.)

I=2–4 A/dm$^2$

Ru from $(NH_3)_4(Ru_2NC_{18}(H_2O)_2)$ or sulfamate

Rh from the sulfate or phosphate with the addition of $H_2SO_4$ pH=1–2

Pd from $Pd(NH_3)_4Br_2$, ETDA,

Pt from $H_2Pt(NO_2)_2SO_4$ with the addition of $NH_4NO_2$, $NH_3$ sulfamate $H_2Pt(NO_2)_2SO_4$ with the addition of $H_2SO_4$ $K_2Pt(OH)_6$ with the addition of KOH and/or ethylamine $H_2PtCl_6$ in acid baths with the addition of HCl Ag: (Ag-110, $t_{1/2}$=250d)

from cyanidic baths with the addition of KOH

Electrochemical Deposition

The labeling of the stent is done by electrochemical deposition of radioactive metal corresponding to its electrochemical potential in terms of the potential of the stent metal. The deposition is performed in a suitable electrolyte and under selected reaction conditions. An especially suitable electrolyte is hydrochloric acid at the concentrations of 0.75 N and 1 N. In this way, all radioisotopes of metals, whose electrochemical potential is more positive than that of the stent metal, can be deposited.

It has been shown that after the electrochemical deposition of the radioactive metal, nonspecifically-bonded activity still adheres to the stent to some extent. To remove the latter, the stent is treated with a solution that contains an electrolyte (e.g., NaCl), a reducing agent and a hydroxycarboxylic acid (e.g., $SnCl_2$ and gentisic acid) or an alcohol and lipophilic cations (e.g., alcoholic tetrabutylammonium bromide solution).

Then, the thus produced stent can still be sealed with a polymer. As a polymer, e.g., a polyacrylate is suitable.

All stents can also be coated with two or more different isotopes. In particular, it is possible to apply short-lived and long-lived isotopes together on a stent (for example, $^{55}Co$ with $^{55}Fe$ or $^{99}Mo$ with $^{57}Co$).

With the described process, it is possible to produce radioactive stents that contain on the surface at least one radioisotope of elements Ag, Au, Bi, Co, Cr, Cu, Fe, Gd, Hg, Ho, In, Ir, Lu, Mn, Ni, Pb, Pd, Pm, Pt, Re, Rh, Ru, Sc, Sm, Tb, Tc or Y.

The invention therefore relates to such stents, as well as the processes for their production. The operations that are necessary for implementing the above processes that are described in principle are known to one skilled in the art. Special embodiments are described in detail in the examples.

The stents according to the invention achieve the above-described object. Stents can be radiolabled easily by the disclosed processes and metered precisely. The stents according to the invention are readily physiologically compatible. As it was possible to show in the animal model, the restenosis is significantly inhibited after balloon denudation by implantation of the stent according to the invention.

The special advantage of the stent according to the invention is that the physician can select on the spot a (non-radioactive) stent according to his needs and can then activate the selected stent by the described process. The few substances and solutions that are required for this purpose can be supplied prepared accordingly, so that the corresponding physician need only immerse the uncoated stent in the individual solutions in the specific sequence. The invention thus also relates to those substances, solutions and preparations (kits) that are prepared for the processes according to the invention.

Embodiments

The following examples are to explain the subject of the invention, without intending that it be limited to these examples.

EXAMPLE 1

Y-90-Direct Labeling of a Wiktor Stent

A Wiktor stent (22.85 mg, model 6570, Medtronic) is covered with a layer of 2 ml of saturated sodium oxalate solution. 37 MBq of yttrium-90-trichloride solution is added and heated for 30 minutes to 60° C. Then, the stent is removed and washed three times with 5 ml of 0.9% sodium chloride solution. The thus labeled Wiktor stent carries an activity of 0.88 MBq of Y-90.

EXAMPLE 2

Tc-99m-Coating of Strecker Stents

A strecker stent (6.51 mg, SS/5-4, Boston Scientific) is covered with a layer of 726 $\mu l$ of sodium pertechnetate solution (231.9 MBq). 100 $\mu l$ of tin(II)-chloride dihydrate solution (5 mg of $SnCl \cdot 2H_2O$/1 ml of 0.01 M HCl) is added, the reaction mixture is put into an ultrasound bath for 5 minutes and finally incubated for 25 minutes at room temperature. The stent is dried and washed three times for 15 minutes with 726 $\mu l$ of 0.9% sodium chloride solution. Finally, it is again covered with a layer of 726 $\mu l$ of 0.9% sodium chloride solution, and the reaction mixture is put into an ultrasound bath for 5 minutes. The dried Strecker stent caries an activity of 1.1 MBq-Tc-99m/6.51 mg (≡29.7 $\mu Ci$/6.51 mg≡4.6 $\mu Ci$/1 mg).

EXAMPLE 3

Re-186 Coating of Strecker Stents

A Strecker stent (6.60 mg, SS/5-4, Boston Scientific) is covered with a layer of 736 $\mu l$ of sodium perrhenate solution (240.2 MBq). 100 $\mu l$ of tin(II)-chloride-dihydrate solution (5 mg of $SnCl_2 \cdot 2H_2O$/1 ml of 0.01 M HCl) is added, the reaction mixture is put into an ultrasound bath for 5 minutes and finally incubated for 25 minutes at room temperature. The stent is dried and washed three times for 15 minutes with 736 $\mu l$ of 0.9% sodium chloride solution. Finally, it is again covered with a layer of 736 $\mu l$ of 0.9% sodium chloride solution, and the reaction mixture is put into an ultrasound bath for 5 minutes. The dried Strecker stent carries an activity of 1.0 MBq-Re-186/6.6 mg (≡27 $\mu Ci$/6.6 mg≡4.1 $\mu Ci$/1 mg).

EXAMPLE 4

Tc-99m Coating of Strecker Stents

A Wiktor stent (22.92 mg, model 6570, Medtronic) is covered with a layer of 2.56 ml of sodium pertechnetate solution (911.5 MBq). 256 $\mu l$ of tin(II)-chloride-dihydrate solution (5 mg of $SnCl_2 \cdot 2H_2O$/1 ml of 0.01 M HCl) is added, the reaction mixture is put into an ultrasound bath for 5 minutes and then incubated for 25 minutes at room temperature. The stent is dried and washed three times for 15 minutes with 2.56 ml of 0.9% sodium chloride solution. Finally, it is again covered with a layer of 2.56 ml of 0.9% sodium chloride solution, and the reaction mixture is put into an ultrasound bath for 5 minutes. The dried Wiktor stent carries an activity of 5.9 MBq-Tc-99m/22.92 mg (≡159.5 $\mu Ci$/22.92 mg≡6.9 $\mu Ci$/1 mg).

EXAMPLE 5

Re-186 Coating of Wiktor Stents

A Wiktor stent (22.31 mg, model 6570, Medtronic) is covered with a layer of 2.5 ml of sodium perrhenate solution (884.1 MBq). 249 $\mu l$ of tin(II) chloride dihydrate solution (5 mg of $SnCl2 \cdot 2H_2O$/1 ml of 0.01 M HCl) is added, the reaction mixture is put into an ultrasound bath for 5 minutes and finally incubated for 25 minutes at room temperature. The stent is dried and washed three times for 15 minutes with 2.5 ml of 0.9% sodium chloride solution. Finally, it is again covered with a layer of 2.5 ml of 0.9% sodium chloride solution, and the reaction mixture is put into an ultrasound bath for 5 minutes. The dried Wiktor stent carries an activity of 5.2 MBq-Re-186/22.31 mg (≡140.5 μCi/22.31 mg≡6.3 μCi/1 mg).

EXAMPLE 6

Administration of a Wiktor Stent that Is Coated with Tc-99m in the Abdominal Aorta of Rabbits The Wiktor stent (model 6570, Medtronic) was coated with Tc-99m as described in Example 4. In an anesthetized (Rompun/Ketavet 1:2) white New Zealand rabbit (3.2 kg of body weight), the femoral artery was exposed. The labeled Wiktor stent was inserted into the vessel via a 5 F sluice and secured in the infrarenal aorta by inflating the balloon catheter. The catheter was then removed, and both the femoral artery and the wound were sutured. Over a period of 8 hours after administration of the stent, whole-body scintigrams were prepared with the aid of a commercially available gamma camera. Five hours after administration of the stent, a scintigram was prepared. Activity could only be located in the area of the stent that is in the infrarenal aorta of the animal. During the entire examination period, no detectable activity was rinsed from the stent. After 8 hours, the rabbit was killed, the stent was removed, and the activity was measured in the gamma counter. The activity that adheres to the stent was equally as high as at the beginning of the test, taking into consideration the radioactive decomposition of $^{99m}$Tc into $^{99}$Tc.

EXAMPLE 7

Labeling of a Strecker Stent with Cu-67

A Strecker stent (1993 mg) in an alkaline copper sulfate/potassium-sodium tartrate solution with an activity of 47.3 MBq is added to a cementation cell (FIG. 2a). After formaldehyde solution is added, the deposition of elementary copper is carried out. The active solution is removed, and the stent is washed four times with physiological common salt solution. It shows an activity of 1.63 MBq.

| | |
|---|---|
| Cu SO$_4$.5H$_2$O | 500 g/100 ml |
| KNaC$_4$H$_4$O$_6$.4H$_2$O | 2500 mg/100 ml |
| NaOH | 700 mg/100 ml |
| HCOH (37%) | 1 ml/100 ml |
| T | 20° C. |

EXAMPLE 8

Labeling of a Nitinol Stent with Au-199

A nitinol stent (496 mg) in a solution that consists of potassium-gold cyanide (K [$^{99}$Au(CN)$_4$]) with an activity of 137.8 MBq, potassium cyanide and potassium hydroxide is added to a cementation cell (FIG. 2b). After being heated to 75° C., potassium borohydride is added and stirred for 3 minutes. After 4 minutes, the solution is drained off, and the stent is washed four times with physiological common salt solution. Its activity is 1.31 MBq.

| | |
|---|---|
| K [Au (CN)$_2$] | 580 mg/100 ml |
| K CN | 1300 mg/100 ml |
| K OH | 1120 mg/100 ml |
| K BH$_4$ | 2160 mg/100 ml |

EXAMPLE 9

Labeling of a Strecker Stent with Ag-110

A Strecker stent (997 mg) in a solution that consists of sodium-silver cyanide (Na Ag (CN)$_2$) with an activity of 40 MBq/mg of stent, sodium cyanide, sodium hydroxide and is added to a cementation cell. After being heated to 55° C., dimethylborane is added. It is stirred for 4 minutes at 55° C., then the solution is drained off, the stent is washed four times with physiological common salt solution, and the activity is determined. It is 1.34 MBq.

| | |
|---|---|
| Na [Ag (CN)$_2$] | 183 mg/100 ml |
| Na CN | 100 mg/100 ml |
| Na OH | 75 mg/100 ml |
| K BH$_4$ | 200 mg/100 ml |
| Na [Ag(CN)$_2$]: | 134 mg of AgCN + 49 mg of NaCN |

EXAMPLE 10

Labeling of a Strecker Stent with Pd/P-32

A Strecker stent (1996 mg) in a solution that consists of palladium chloride, hydrochloric acid, ammonia and ammonium chloride is added to a cementation cell (FIG. 2a). The solution has a temperature of 55° C. and is stirred. 9 mg of sodium hypophosphite-monohydrate, which has an activity of 36.4 MBq, is stirred into the solution. A palladium-phosphorus alloy, which has an activity of 1.31 MBq, is deposited on the stent.

| | |
|---|---|
| Pd Cl$_2$ | 200 mg/100 ml |
| HCl (38%) | 0.4 ml/100 ml |
| NH$_4$OH (28%) | 16 ml/100 ml |
| NH$_4$Cl | 2.7 g/100 ml |
| NaH$_2$PO$_2$.H$_2$O | 1 g/100 ml |
| T | 55° C. |

3 g of hypophosphite yields 1 g of Pd alloy with 1.5% P

EXAMPLE 11

Labeling of a High-grade Steel Stent with Pd/P-32

A high-grade steel stent (498 mg) in a solution that consists of palladium chloride, hydrochloric acid, ammonia and ammonium chloride is added to a cementation cell (FIG. 2b). The solution has a temperature of 55° C. and is stirred. 6 mg of sodium hypophosphite-monohydrate, which has an activity of 37.8 MBq, is stirred into the solution. A palladium-phosphorus alloy, which has an activity of 1.16 MBq, is deposited on the stent.

| | |
|---|---|
| Pd Cl$_2$ | 200 mg/100 ml |
| HCl (38%) | 0.4 ml/100 ml |
| NH$_4$OH (28%) | 16 ml/100 ml |
| NH$_4$Cl | 2.7 g/100 ml |
| NaH$_2$PO$_2$.H$_2$O | 1 g/100 ml |
| T | 55° C. |
| 3 g of hypophosphite yields 1 g of Pd alloy with 1.5% P | |

EXAMPLE 12

Labeling of a Nitinol Stent with Pd/P-32

A nitinol stent (96 mg) in a solution that consists of palladium chloride, hydrochloric acid, ammonia and ammonium chloride is brought into a cementation cell (FIG. 2b). The solution has a temperature of 55° C. and is stirred. 3 mg of sodium hypophosphite-monohydrate, which has an activity of 39.4 MBq, is stirred into the solution. A palladium-phosphorus alloy, which has an activity of 1.37 MBq, is deposited on the stent.

| | |
|---|---|
| Pd Cl$_2$ | 200 mg/100 ml |
| HCl (38%) | 0.4 ml/100 ml |
| NH$_4$OH (28%) | 16 ml/100 ml |
| NH$_4$Cl | 2.7 g/100 ml |
| NaH$_2$PO$_2$.H$_2$O | 1 g/100 ml |
| T | 55° C. |
| 3 g of hypophosphite yields 1 g of Pd-alloy with 1.5% P | |

EXAMPLE 13

Labeling of a High-grade Steel Stent with P-32

A high-grade steel stent (1992 mg) in a solution of phosphoric acid that is heated to 50° C. with a $^{32}$P activity of 41.4 MBq is brought into a galvanization cell (FIG. 1). The stent is operated as an anode, and electrolysis is done for 2 minutes at 2 V. Then, the solution is drained off, the stent is rinsed four times with physiological common salt solution, and the activity of the stent is measured. It is 0.93 MBq.

EXAMPLE 14a

Coating of a Wiktor Stent with 1-{3-[N-(2-methoxyethyl)-octadecylsulfamoyl]-2-hydroxypropyl}-4,7,10-tris-(hydroxycarbonylmethyl)-1,4,7,10-tetraazacyclododecane 50 mg of 1-{3-[N-(2-methoxyethyl)-octadecylsulfamoyl]-2-hydroxypropyl}-4,7,10-tris-(hydroxycarbonylmethyl)-1,4,7,10-tetraazacyclododecane (produced according to DE 43 40 809.5) is dissolved in 1 ml of ethanol. The Wiktor stent (22.82 mg, model 6570, Medtronic) is covered with a layer of the solution that is thus produced. Then, 2 ml of water is added and incubated for 15 minutes in an ultrasound bath. The Wiktor stent is removed and dried.

EXAMPLE 14b

In-111 Labeling of a Wiktor Stent that Is Coated with 1-{3-[N-(2-Methoxyethyl)-octadecylsulfamoyl]-2-hydroxypropyl}-4,7,10-tris-(hydroxycarbonylmethyl)-1,4,7,10-tetraazacyclododecane A Wiktor stent that is coated as under Example 14a with 1-{3-[N-(2-methoxyethyl)-octadecylsulfamoyl]-2-hydroxypropyl}-4,7,10-tris-(hydroxycarbonylmethyl)-1,4,7,10-tetraazacyclododecane (produced according to DE 43 40 809.5) is covered with a layer of 2 ml of 0.9% sodium chloride solution. After 37 MBq of indium-trichloride solution is added, the reaction mixture is put into an ultrasound bath for 15 minutes. The stent is removed, the latter is washed three times with 5 ml of 0.9% sodium chloride solution and dried. The Wiktor stent that is thus labeled carries an activity of 1.49 MBq of In-111.

EXAMPLE 14c

Y-90 Labeling of a Wiktor Stent that Is Coated with 1-{3-[N-(2-Methoxyethyl)-octadecylsulfamoyl]-2-hydroxypropyl}-4,7,10-tris-(hydroxycarbonylmethyl)-1,4,7,10-tetraazacyclododecane A Wiktor stent that is coated with 1-{3-[N-(2-methoxyethyl)-octadecylsulfamoyl]-2-hydroxypropyl}-4,7,10-tris-(hydroxycarbonylmethyl)-1,4,7,10-tetraazacyclododecane (produced according to DE 43 40 809.5) as under Example 14a is covered with a layer of 2 ml of 0.9% sodium chloride solution. After 37 MBq of yttrium-90-trichloride solution is added, the reaction mixture is put into an ultrasound bath for 15 minutes. The stent is removed, the latter is washed three times with 5 ml of 0.9% sodium chloride solution and dried. The Wiktor stent that is thus labeled carries an activity of 1.12 MBq of Y-90.

EXAMPLE 15a

1-{3-[N-(2-Methoxyethyl)-octadecylsulfamoyl]-2-hydroxypropyl}-4,7,10-tris-(hydroxycarbonylmethyl)-4,7,10-tetraazacyclododecane, Y-90 Complex 50 mg of 1-{3-[N-(2-methoxyethyl)-octadecylsulfamoyl]-2-hydroxypropyl}-4,7,10-tris-(hydroxycarbonylmethyl)-1,4,7,10-tetraazacyclododecane (produced according to DE 4340809.5) is dissolved in 1 ml of ethanol. After 37 MBq of yttrium-90-trichloride solution is added, the reaction mixture is refluxed for 10 minutes. The Y-90 complex solution that is thus prepared can be used without further purification for coating a Wiktor stent.

EXAMPLE 15b

Y-90-Labeling of a Wiktor Stent with the Y-90 Complex of 1-{3-[N-(2-Methoxyethyl)-octadecylsulfamoyl]-2-hydroxypropyl}-4,7,10-tris-(hydroxycarbonylmethyl)-1,4,7,10-tetraazacyclododecane A Wiktor stent (22.89 mg, model 6570, Medtronic) is added to 900 µl of the solution, produced under Example 15a, of 1-{3-[N-(2-methoxyethyl)-octadecylsulfamoyl]-2-hydroxypropyl}-4,7,10-tris-(hydroxycarbonylmethyl)-1,4,7,10-tetraazacyclododecane-Y-90-complex. After 2 ml of water is added, the reaction mixture is put into an ultrasound bath for 15 minutes. Then, the Wiktor stent is removed and washed three times with 5 ml of 0.9% sodium chloride solution. The Wiktor stent that is thus labeled carries an activity of 0.98 MBq of Y-90.

EXAMPLE 16a

N,N'-Bisundecyl-diethylene-triamine-pentaacetic Acid-diamide 3.57 g (10 mmol) of diethylene-triamine-pentaacetic acid-bisanhydride is suspended together with 4.05 g (40 mmol) of triethylamine in 100 ml of absolute dimethylformamide. Then, a solution of 3.42 g (20 mmol) of undecylamine, dissolved in 50 ml of absolute dichloromethane, is added in drops to the reaction mixture at room temperature. The reaction batch is stirred for 6 hours at room temperature, filtered and concentrated by evaporation in a medium-high vacuum. The residue is dissolved three times in 100 ml of dimethylformamide and in each case concentrated by evaporation in a medium-high vacuum. 50 ml of absolute diethyl ether is poured over the foamy reaction product and stirred overnight. It is filtered and dried in a medium-high vacuum.

Yield: 6.3 g (90%), white powder.

Elementary analysis:

| Cld: | C 61.77 | H 9.94 | N 10.01 | O 18.86 |
|---|---|---|---|---|
| Fnd: | C 61.52 | H 9.63 | N 9.91 | O |

EXAMPLE 16b

Coating of a Wiktor Stent with N,N'-Bisundecyl-diethylene-triamine-pentaacetic Acid-diamide 50 mg of N,N'-bisundecyl-diethylene-triamine-pentaacetic acid-diamide (produced according to Example 16a) is dissolved in 1 ml of ethanol. The Wiktor stent (22.93 mg, model 6570, Medtronic) is covered with a layer of the solution that is thus produced. Then, 2 ml of water is added and it is incubated for 15 minutes in an ultrasound bath. The Wiktor stent is removed and dried.

EXAMPLE 16c

In-111-Labeling of a Wiktor Stent that Is Coated with N,N'-Bisundecyl-diethylene-triamine-pentaacetic Acid-diamide A Wiktor stent that is coated with N,N'-bisundecyl-diethylene-triamine-pentaacetic acid-diamide as under Example 16b is covered with a layer of 2 ml of 0.9% sodium chloride solution. After 37 MBq of indium-trichloride solution is added, the reaction mixture is put into an ultrasound bath for 15 minutes. The stent is removed, the latter is washed three times with 5 ml of 0.9% sodium chloride solution and dried. The Wiktor stent that is thus labeled carries an activity of 1.34 MBq of In-111.

EXAMPLE 16d

Y-90-Labeling of a Wiktor Stent that Is Coated with N,N'-Bisundecyl-diethylene-triamine-pentaacetic Acid-diamide A Wiktor stent that is coated with N,N'-bisundecyl-diethylene-triamine-pentaacetic acid-diamide as under Example 16b is covered with a layer of 2 ml of 0.9% sodium chloride solution. After 37 MBq of yttrium-trichloride solution is added, the reaction mixture is put into an ultrasound bath for 15 minutes. The stent is removed, the latter is washed three times with 5 ml of 0.9% sodium chloride solution and dried. The Wiktor stent that is thus labeled carries an activity of 1.11 MBq of Y-90.

EXAMPLE 17a

N,N'-Bisundecyl-diethylene-triamine-pentaacetic Acid-diamide, Y-90 Complex 50 mg of N,N'-bisundecyl-diethylene-triamine-pentaacetic acid-diamide (Example 4a) is dissolved in 1 ml of ethanol. After 37 MBq of yttrium-90-trichloride solution is added, the reaction mixture is heated for 10 minutes to 60° C. The Y-90-complex solution that is thus prepared can be used without further purification for coating a Wiktor stent.

EXAMPLE 17b

Y-90-Labeling of a Wiktor Stent with the Y-90 Complex of N,N'-Bisundecyl-diethylene-triamine-pentaacetic Acid-diamide A Wiktor stent (22.87 mg, model 6570, Medtronic) is added to 900 µl of the solution, produced under Example 17a, of the Y-90 complex of N,N'-bisundecyl-diethylene-triamine-pentaacetic acid-diamide. After 2 ml of water is added, the reaction mixture is put into an ultrasound bath for 15 minutes. Then, the Wiktor stent is removed and washed three times with 5 ml of 0.9% sodium chloride solution. The Wiktor stent that is thus labeled carries an activity of 0.99 MBq of Y-90.

EXAMPLE 18a

N-Benzyloxycarbonyl-glycyl-N'-undecyl-glycinamide 3.63 g (10 mmol) of N-benzyloxycarbonyl-glycyl-glycine-N-hydroxysuccinimide ester and 1.71 g (10 mmol) of undecylamine are dissolved in 100 ml of absolute dichloromethane. The reaction mixture is stirred for 6 hours at room temperature. Then, it is diluted with 100 ml of dichloromethane, the organic phase is washed twice with 50 ml of saturated sodium bicarbonate solution and once with 50 ml of water. It is dried on magnesium sulfate, and the solvent is evaporated in a vacuum. The crude product is purified by chromatography on silica gel (eluant: dichloromethane/methanol 95:5).

Yield: 3.8 g (90.6%), white powder

| Elementary analysis: | Cld: | C 65.84 | H 8.89 | N 10.01 | O 15.25 |
|---|---|---|---|---|---|
| | Fnd: | C 65.71 | H 9.02 | N 10.10 | O |

EXAMPLE 18b

Glycyl-N'-undecyl-glycinamide 3 g (7.15 mmol) of N-benzyloxycarbonyl-glycyl-N'-undecyl-glycinamide (Example 18a) is dissolved in 100 ml of absolute ethanol. After 300 mg of palladium is added to carbon (10%), it is hydrogenated for 2 hours at room temperatur (1 atmosphere of hydrogen). It is filtered and concentrated by evaporation in a vacuum. The resulting amine is used without further purification for the subsequent reaction.

Yield: 1.92 g (94.1%), white foam.

| Elementary analysis: | Cld: | C 63.12 | H 10.95 | N 14.72 | O 11.21 |
|---|---|---|---|---|---|
| | Fnd: | C 63.03 | H 11.04 | N 14.57 | O |

EXAMPLE 18c

N-(S-Acetyl-mercaptoacetyl)-glycyl-N'-undecyl-glycinamide 285.4 mg (1 mmol) of glycyl-N'-undecyl-glycinamide (Example 18b) and 231.2 mg (1 mmol) of S-acetylmercapto-acetic acid-N-hydroxy-succinimide ester are dissolved together in 20 ml of absolute dichloromethane. The reaction mixture is stirred for 6 hours at room temperature. Then, it is diluted with 20 ml of dichloromethane, the organic phase is washed twice with 5 ml of semisaturated sodium bicarbonate solution and washed once with 5 ml of water. It is dried on magnesium sulfate, and the solvent is evaporated in a vacuum. The crude product is purified by chromatography on silica gel (eluant: dichloromethane/methanol 93:7).

Yield: 362 mg (90.1%), white powder.

| EA: | Cld: | C 56.83 | H 8.79 | N 10.46 | O 15.94 | S 7.98 |
|---|---|---|---|---|---|---|
| | Fnd: | C 56.67 | H 8.93 | N 10.18 | O | S 7.72 |

EXAMPLE 18d

N-(Mercaptoacetyl)-glycyl-N'-undecyl-glycinamide 201 mg (0.5 mmol) of N-(S-acetyl-mercaptoacetyl-glycyl-N'-undecyl-glycinamide (Example 18c) is dissolved in 15 ml of absolute ethanol. It is saturated with argon, and an ammonia stream is directed through the solution for 30 minutes. Then, it is concentrated by evaporation, and the residue is taken up in 20 ml of dichloromethane. The organic phase is shaken once with 2% aqueous citric acid and dried on sodium sulfate. The solvent is evaporated in a vacuum, and the residue is chromatographed on silica gel (eluant: dichloromethane/methanol 9:1).

Yield: 153 mg (85.1%), white powder.

| EA: | Cld: | C 56.79 | H 9.25 | N 11.69 | O 13.35 | S 8.92 |
|---|---|---|---|---|---|---|
| | Fnd: | C 56.67 | H 9.43 | N 11.48 | O | S 8.71 |

EXAMPLE 18e

Coating of a Wiktor Stent with N-(Mercaptoacetyl)-glycyl-N'-undecyl-glycinamide 50 mg of N-(mercaptoacetyl)-glycyl-N'-undecyl-glycinamide (Example 18d) is dissolved in 1 ml of ethanol. The Wiktor stent (22.89 mg, model 6570, Medtronic) is covered with a layer of the solution that is thus produced. Then, 2 ml of water is added, and it is incubated for 15 minutes in an ultrasound bath. The Wiktor stent is removed and dried.

EXAMPLE 18f

Re-186-Labeling of a Wiktor Stent that is Coated with N-(Mercaptoacetyl)-glycyl-N'-undecyl-glycinamide A Wiktor stent that is coated with N-(mercaptoacetyl)-glycyl-N'-undecyl-glycinamide, as under Example 18e, is covered with a layer of 2 ml of disodium hydrogen phosphate buffer (0.1M, pH=8.5). After 37 MBq of perrhenate solution is added, 100 µl of tin dichloride-dihydrate solution (5 mg of SnCl2×2H2O/1 ml of 0.1 M HCl) is added to the reaction batch. The reaction mixture is put into an ultrasound bath for 15 minutes. The stent is to removed, the latter is washed three times with 5 ml of 0.9% sodium chloride solution and dried. The Wiktor stent that is thus labeled carries an activity of 1.31 MBq of Re-186.

EXAMPLE 18g

N-(Mercaptoacetyl)-glycyl-N'-undecyl-glycinamide, Re-186 Complex 5 mg of N-(mercaptoacetyl)-glycyl-N'-undecyl-glycinamide (Example 18d) is dissolved in 800 µl of ethanol. After 5 mg of disodium-L-tartrate and 50 µl of 0.1M sodium hydrogen phosphate buffer (pH=8.5) are added, 37 MBq of perrhenate and 100 µl of tin dichloride-dihydrate solution (5 mg of SnCl2×2H2O/1 ml of 0.1 M HCl) are added. The reaction mixture is heated for 5 minutes to 60° C. The solution of the Re-186 complex of N-(mercaptoacetyl)-glycyl-N'-undecyl-glycinamide that is thus prepared can be used directly for labeling a Wiktor stent.

EXAMPLE 18h

Labeling of a Wiktor Stent with the Re-186 Complex of N-(Mercaptoacetyl)-glycyl-N'-undecyl-glycinamide A Wiktor stent (22.99 mg, model 6570, Medtronic) is added to 900 µl of the solution, produced under Example 18g, of the Re-186 complex of N-(mercaptoacetyl)-glycyl-N'-undecyl-glycinamide. After 2 ml of water is added, the reaction mixture is put into an ultrasound bath for 15 minutes. Then, the Wiktor stent is removed and washed three times with 5 ml of 0.9% sodium chloride solution. The Wiktor stent that is thus labeled carries an activity of 1.13 MBq of Re-186.

EXAMPLE 19

Y-90-Direct Labeling of a Wiktor Stent

A Wiktor stent (22.85 mg, model 6570, Medtronic) is covered with a layer of 2 ml of saturated sodium oxalate solution. 37 MBq of yttrium-90-trichloride solution is added and heated for 30 minutes to 60° C. Then, the stent is removed and washed three times with 5 ml of 0.9% sodium chloride solution. The Wiktor stent that is thus labeled carries an activity of 0.88 MBq of Y-90.

EXAMPLE 20

Use of Bisdecyloylhydrazino-diethylenetriamine-pentaacetate for Coating Stents

EXAMPLE 20a

Production of Bisdecyloylhydrazino-diethylenetriamine-pentaacetate 17.5 g of decanoic acid methyl ester is dissolved in 1 l of absolute ethanol and mixed with 350 ml of hydrazine hydrate. It is refluxed for 3 hours and then stirred overnight at room temperature. The solution is concentrated by evaporation to about 300 ml and allowed to stand until the product is crystallized out. After it is filtered off and dried, 16.6 g (=94% of theory) of decanoic acid hydrazide is obtained.

| Elementary analysis: | C | H | N | O |
|---|---|---|---|---|
| Calculated: | 64.5% | 11.9% | 15.0% | 8.6% |
| Found: | 65.4% | 11.9% | 14.5% | |

3.6 g of diethylenetriamine-pentaacetic acid-bisanhydride is dissolved in 500 ml of DMF and mixed under nitrogen atmosphere with 4.2 ml of triethylamine and 3.7 g of decanoic acid hydrazide. It is stirred for 24 hours at room temperature and then undissolved components are filtered off. The solution is concentrated by evaporation, and the oily residue is taken up in 500 ml of ether. After 500 ml of hexane is added and stirring is continued, the product precipitates in crystalline form. After drying, 1.2 g (=95% of theory) of bisdecyloylhydrazino-diethylene-triamine-pentaacetate is obtained.

EXAMPLE 20b

Coating of the Strecker Stent with Bisdecyloylhydrazino-diethylenetriamin-pentaacetate 2 mg of bisdecyloylhydrazino-diethylenetriamine-pentaacetate is dissolved in 1 ml of methanol and precipitated with the addition of 2 ml of hexane. In this suspension, a Strecker stent 0.5 cm in length (SS/5-4, Boston Scientific) is immersed and incubated for 15 minutes by means of ultrasound. The stent is then taken out and dried. This process is repeated five times, and finally excess coating material is removed by washing with physiological common salt solution in an ultrasound bath.

EXAMPLE 20c

Labeling of Strecker Stents that are Coated with Bisdecyloylhydrazino-diethylenetriamine-pentaacetate The thus treated stent was immersed for labeling in a commercially acquired solution of the radioactive metal isotope (In-111, Y-90, 74 MBq each) and incubated for 15 minutes in an ultrasound bath. Finally, it was washed in physiological saline for 20 minutes in an ultrasound bath. 0.3 MBq of residual activity remains on the stent.

EXAMPLE 20d

Coating of Strecker Stents with Labeled Bisdecyloylhydrazino-diethylenetriamine-pentaacetate 2 mg of bisdecyloylhydrazino-diethylenetriamine-pentaacetate is dissolved in 1 ml of methanol and labeled with a commercially acquired solution of the radioactive metal isotope (In-111, Y-90, 74 MBq each). In this solution, a Strecker stent 0.5 cm in length (SS/5-4, Boston Scientific) is immersed and incubated for 15 minutes by means of ultrasound. Then, the stent was taken out and dried. This process was repeated 5 times, and finally soluble activity was removed by washing with physiological common salt solution in an ultrasound bath. 0.1 MBq of residual activity remains on the stent.

EXAMPLE 21a

Use of Thioacetyl-Gly-Gly-amidoethyl-PEG-methylether for Coating Stents

Production of Thioacetyl-Gly-Gly-amidoethyl-PEG-methylether 50 g of aminoethyl-polyethyleneglycol-methylether with a molecular weight of about 5000 is stirred with 3.6 g of N-benzyloxycarbonyl-glycylglycine-N-hydroxysuccinimide ester (Z-Gly-Gly-OSu) in 100 ml of DMF for 24 hours at room temperature. The solution is concentrated by evaporation, and the residue is further reacted without further purification.

The residue is dissolved in a mixture of methanol/water 1:1, mixed with 2 g of palladium on activated carbon and hydrogenated under hydrogen atmosphere (pressure 1 bar) until about 230 ml of hydrogen is taken up. Then, the catalyst is filtered off, and the remaining mixture is purified after concentration by evaporation with a gel filtration. After drying, 49 g (=96% of theory) of glycyl-glycyl-amidoethyl-PEG-methylether is obtained.

This product is dissolved in 100 ml of DMF and stirred with 2.2 g of S-acetyl-thioglycolic acid-N-hydroxysuccinimide ester for 24 hours at room temperature. Then, the mixture is mixed with 20 ml of aqueous ammonia solution and stirred for 2 more hours. The product is acidified to pH 4 with aqueous 6 N hydrochloric acid and concentrated by evaporation. The purification is carried out on a gel filtration column. 42 g (=85% of theory) of thioacetyl-glycyl-glycyl-amidoethyl-polyethyleneglycol-methyl ester is obtained.

EXAMPLE 21b

Coating of Strecker Stents with Thioacetyl-Gly-Gly-amidoethyl-PEG-methylether and Subsequent Radiolabeling 2 mg of thioacetyl-Gly-Gly-amidoethyl-PEG-methylether with a molecular weight of about 5300 was dissolved in 2 ml of methanol, precipitated with the addition of 1 ml of hexane, a Strecker stent 0.5 cm in length (SS/5-4, Boston Scientific) was immersed in this suspension and incubated by means of ultrasound for 15 minutes. Then, the stent was taken out and dried. This process was repeated five times, and finally excess coating material was removed by washing with physiological common salt solution in an ultrasound bath.

The thus treated stent was immersed for labeling in a solution of the radioactive metal isotope (Tc-99m, Re-186) that consists of 5 ml of the solution (Tc-99m from the generator, Re-186 that was acquired commercially and contained about 3 MBq of activity), 200 $\mu$l of phosphate buffer ($Na_2HPO_4$, 0.5 mol/l, pH 8.5), 50 $\mu$l of a 0.15 molar disodium tartrate solution and 2.5 $\mu$l of a 0.2 molar $SnCl_2$ solution and incubated for 15 minutes in an ultrasound bath. Finally, it was washed in physiological saline for 20 minutes in an ultrasound bath. 0.1 MBq of residual activity remains on the stent.

EXAMPLE 21c

Coating of Strecker Stents with Radiolabeled Thioacetyl-Gly-Gly-amidoethyl-PEG-methylether 0.5 mg of thioacetyl-Gly-Gly-amidoethyl-PEG-methylether with a molecular weight of about 5300 was dissolved in 300 $\mu$l of phosphate buffer ($Na_2HPO_4$, 0.5 mol/l, pH 8.5), and 50 $\mu$l of a 0.15 molar disodium tartrate solution and 2.5 $\mu$l of a 0.2 molar $SnCl_2$ solution were added. The mixture was mixed with a pertechnetate solution (2 MBq) from a Tc-99m generator and incubated for 15 minutes at 60° C. A solution of polyethylene glycols that are labeled with Re-186 could be produced analogously.

A Strecker stent 0.5 cm in length (SS/5-4, Boston Scientific) was immersed in this solution and incubated for 15 minutes by means of ultrasound. Then, the stent was taken out and dried. This process was repeated several times in succession, until the adhering activity had reached 0.3

MBq. Then, it was washed twice for 60 minutes in physiological saline. A residual activity of 100 KBq remained.

example 22

Coating of Strecker Stents with Tc-99m-Asp-Gly-Gly-Cys-Gly-Cys-Phe-(Dr-Trp)-Leu-Asp-Ile-Ile-Trp 0.5 mg of the Asp-Gly-Gly-Cys-Gly-Cys-Phe-(D-Trp)-Leu-Asp-Ile-Ile-Trp that was produced analogously to Barany and Marrifield, The Peptides; Analysis, Biology, Academic Press, New York, 1990; Stewart and Young, Solid-Phase Peptide Synthesis, 2nd Edition, Pierce Chemical Co., Rockford, Ill. 1984 is dissolved in 300 ml of phosphate buffer ($Na_2HPO_4$, 0.5 mol/l, pH 8.5) and mixed with 50 $\mu$l of a 0.15 molar disodium-L-tartrate solution, 2.5 $\mu$l, of a 0.2 molar tin(II) chloride-dihydrate solution. The reaction mixture is mixed with a pertechnetate solution (50 mCi=1.85 GBq) from an Mo-99/Tc-99m-generator and incubated for 10 minutes at room temperature.

A Strecker stent 0.5 cm in length (SS/5-4, Boston Scientific) was incubated five times in succession for 15 minutes each in the Tc-99m-peptide solution. After each incubation, the activity that adheres to the stent was determined with the aid of a commercially available gamma counter. As the figure shows, an activity of 230 $\mu$Ci on the Strecker stent remained even after one-time incubation.

The repetitions of this incubation do not result in any significantly higher activity that remains on the stent. The stent that was coated with the Tc-99m-peptide solution was then washed four times every minute and twice for 60 minutes in physiological saline. After the first rinsing, 81 $\mu$Ci still remains on the stent. The additional rinsing processes did not result in any significant reduction of the activity that is bonded to the stent.

EXAMPLE 23

Tc-99m-Coating of Strecker Stents

A Wiktor stent (22.92 mg, model 6570, Medtronic) is covered with a layer of 2.56 ml of sodium-pertechnetate solution (911.5 MBq). 256 $\mu$l of tin(II) chloride-dihydrate solution (5 mg of $SnCl_2 \cdot 2H_2O$/1 ml of 0.01 M HCl) is added, the reaction mixture is put into an ultrasound bath for 5 minutes and finally incubated for 25 minutes at room temperature. The stent is dried and washed three times for 15 minutes with 2.56 ml of 0.9% sodium chloride solution. Finally, it is again covered with a layer of 2.56 ml of 0.9% sodium chloride solution, and the reaction mixture is put into an ultrasound bath for 5 minutes. The dried Wiktor stent carries an activity of 5.9 MBq-Tc-99m/22.92 mg ($\equiv$159.5 $\mu$Ci/22.92 mg $\equiv$6.9 $\mu$Ci/1 mg).

EXAMPLE 24

Re-186 Coating of Wiktor Stents

A Wiktor stent (22.31 mg, model 6570, Medtronic) is covered with a layer of 2.5 ml of sodium pertechnetate solution (884.1 MBq). 249 $\mu$l of tin(II) chloride-dihydrate solution (5 mg of $SnCl2 \cdot 2H_2O$/1 ml of 0.01 M HCl) is added, the reaction mixture is put into an ultrasound bath for 5 minutes and finally incubated for 25 minutes at room temperature. The stent is dried and washed three times for 15 minutes with 2.5 ml of 0.9% sodium chloride solution. Finally, it is again covered with a layer of 2.5 ml of 0.9% sodium chloride solution, and the reaction mixture is put into an ultrasound bath for 5 minutes. The dried Wiktor stent carries an activity of 5.2 MBq-Re-186/22.31 mg ($\equiv$140.5 $\mu$Ci/22.31 mg$\equiv$6.3 $\mu$Ci/1 mg).

EXAMPLE 25

Administration of a Wiktor Stent that is Coated with Tc-99m in the Abdominal Aorta of Rabbits The Wiktor stent (model 6570, Medtronic) was coated with Tc-99m as described in Example 10. In an anesthetized (Rompun/Ketavet 1:2) white New Zealand rabbit (3.2 kg of body weight), the femoral artery was exposed. The labeled Wiktor stent was inserted into the vessel via a 5 F sluice and secured in the infrarenal aorta by inflating the balloon catheter. The catheter was then removed, and both the femoral artery and the wound were sutured. Over a period of 8 hours after administration of the stent, whole-body scintigrams were prepared with the aid of a commercially available gamma camera. FIG. XI shows a scintigram that was prepared five hours after administration of the stent. Activity could only be located in the area of the stent that is in the infrarenal aorta of the animal. During the entire examination period, no detectable activity was rinsed from the stent. After 8 hours, the rabbit was killed, the stent was removed, and the activity was measured in a gamma counter. The activity that adheres to the stent was equally as high as at the beginning of the test.

EXAMPLE 26a

Cementation of a Strecker Stent with Gold

A Strecker stent (about 200 mg) is coated with gold (2 minutes of 30 mg of gold(III)-chloride in 30 ml of 5% aqueous solution) in a cementation vessel (FIG. 2a). The stent that is thus obtained is washed three times with 10% aqueous nitric acid and twice with water. Then, it is [washed] twice with acetonitrile and dried.

EXAMPLE 26b

Linkage of 11-Amino-undecyl-1-thiol to the Surface 500 mg of 11-aminoundecyl-1-thiol is dissolved in a solution that consists of 10 ml of 7.5% aqueous nitric acid/5 ml of tetrahydrofuran/3 ml of 1,2-dichloromethane. The Strecker stent that is produced from Example 26a is immersed in this solution under protective gas (in an ultrasound bath/37° C.). It is irradiated for about 15 minutes. The stent is washed three times with ethanol, then twice with acetonitrile.

EXAMPLE 26c

Coupling with DTPA-bis-anhydride

The stent that is described in Example 26b is immersed in a 7.5% aqueous sodium carbonate solution, and 500 mg of DTPA-bis-anhydride in 5 portions per 100 mg each is added at 0° C. while being stirred. It is stirred for 10 minutes at 0° C. The stent is washed twice with 5% aqueous hydrochloric acid, then three times with water and twice with acetonitrile.

EXAMPLE 26d

Indium-111-Labeling of the Stent that is Derivatized from DTPA-Amide

The stent that is described in Example 26c is immersed in a solution of acetate buffer (0.001 mol, pH 5.5), and In-111 solution (starting activity: 48.8 MBq) is added. It is stirred for 5 minutes at room temperature. The stent is washed three times with 3% aqueous sodium carbonate solution, then twice with physiological common salt solution. The stent can be used directly for implantation. The stent showed a radioactivity of 1.2 MBq.

EXAMPLE 27a

Coupling of DOTA to the Stent of Example 26b

The stent that is obtained from Example 26b is immersed in a solution of phosphate buffer (0.1 mol/l, pH 7.4), and 150 mg of 1,4,7,10-tetra(carboxymethyl)-1,4,7,10-tetraazacyclododecane (DOTA) is added. It is cooled to 0° C., and 200 mg of N-hydroxysulfosuccinimide (Sulfo-NHS) and 200 mg of 1-ethyl-3-(dimethylaminopropyl)-carbodiimide HCl (EDC) are added. It is stirred for 30 minutes at 0° C. The stent is washed twice with water and twice with physiological common salt solution.

EXAMPLE 27b

Labeling with In-111

The stent that is described in Example 27a is immersed in a solution of acetate buffer (0.01 mol, pH 5), and In-111 solution (starting activity: 37.3 MBq) is added. It is heated for 30 minutes to 50° C. The stent is washed twice with 3% aqueous sodium carbonate solution, then three times with physiological common salt solution. The stent showed a radioactivity of 1.45 MBq.

EXAMPLE 28a

Coupling of 4-Isothiocyanato-benzyl-DTPA to the Stent of Example 26b

A stent that is prepared in Example 26b is immersed in a solution of sodium carbonate buffer (0.1 mol/l, pH 9), and 100 mg of 4-isothiocyanato-benzyl-DTPA (Gansow, O. WO 91/14459) is added. It is stirred for 30 minutes at room temperature. The stent is washed twice with 3% sodium carbonate solution, then three times with physiological common salt solution.

EXAMPLE 28b

Labeling with Cu-67

The stent that is described in Example 28a is immersed in a solution of acetate buffer (0.01 mol, pH 5), and Cu-67 solution (starting activity: 34.5 MBq) is added. It is stirred for 5 minutes at room temperature. The stent is washed twice with 3% aqueous sodium carbonate solution, then three times with physiological common salt solution. The stent showed a radioactivity of 0.98 MBq.

EXAMPLE 29a

Coupling of 4-Isothiocyanato-benzyl-DOTA to the Stent of Example 26b

A stent that is prepared in Example 26b is immersed in a solution of sodium carbonate buffer (0.1 mol/l, pH 9), and 100 mg of 4-isothiocyanato-benzyl-DOTA (Gansow, O. U.S. Pat. No. 4,923,985) is added. It is stirred for 30 minutes at room temperature. The stent is washed twice with 3% sodium carbonate solution, then three times with physiological common salt solution.

EXAMPLE 29b

Labeling with Cu-67

The stent that is described in Example 29a is immersed in a solution of acetate buffer (0.01 mol, pH 5), and Cu-67 solution (starting activity: 28.6 MBq) is added. It is stirred for 15 minutes at 40° C. The stent is washed twice with 3% aqueous sodium carbonate solution, then three times with physiological common salt solution. The stent showed a radioactivity of 0.77 MBq.

EXAMPLE 30a

Bisamide of Cystamine with DTPA 10 g (28 mmol) of DTPA-bis-anhydride is suspended in 100 ml of dimethyl sulfoxide. It is cooled to 0° C. and 5.7 g (56 mmol) of triethylamine is added. Then, 1.58 g (7 mmol) of cystamine dihydrochloride is added, and it is stirred for 24 hours at room temperature. 20 ml of formic acid and 1000 ml of diethyl ether are added. The precipitated solid is filtered off and chromatographed on RP18 (mobile solvent: gradient that consists of acetonitrile/THF/water). The product that is obtained after the main fractions are concentrated by evaporation is recrystallized from a little methanol.

Yield: 1.96 g (31% of theory relative to cystamine) of a colorless, hygroscopic solid.

Water Content: 6.8%

Elementary analysis (relative to anhydrous substance):

| | | | | |
|---|---|---|---|---|
| Cld: | C 42.57 | H 6.03 | N 12.41 | S 7.10 |
| Fnd: | C 42.39 | H 5.97 | N 12.53 | S 7.03 |

EXAMPLE 30b

Coupling of DTPA-Cysteamine Amide to a Gold-Cemented Strecker Stent (26a)

The Strecker stent that is described in Example 26a is fixed in an electrolysis cell (FIG. 1), and a solution of phosphate buffer (0.1 mol/l, pH 5) is added. 100 mg of the title compound of Example 126a is added to the solution, and a voltage of 3 V is applied. Electrolysis is done for 15 minutes at room temperature. The stent is washed four times with water and can be used directly for labeling.

EXAMPLE 30c

Labeling with In-111

The stent that is described in Example 30b is immersed in a solution of acetate buffer (0.01 mol, pH 5), and In-111 solution (starting activity: 34.7 MBq) is added. It is stirred for 5 minutes at room temperature. The stent is washed twice with 3% aqueous sodium carbonate solution, then three times with physiological common salt solution. The stent showed a radioactivity of 1.11 MBq.

EXAMPLE 31

Labeling with Cu-67

The stent that is described in Example 30b is immersed in a solution of acetate buffer (0.01 mol, pH 5), and Cu-67 solution (starting activity: 41.2 MBq) is added. It is stirred for 3 minutes at room temperature. The stent is washed twice with 3% aqueous sodium carbonate solution, then three times with physiological common salt solution. The stent showed a radioactivity of 0.97 MBq.

EXAMPLE 32a

Coupling of N,N-dimethyl-2-(3,3,5,11,13,13-hexamethyl-1,2-dithia-5,8,11-triaza-cyclotridecan-8-yl)-ethylamine to a Gold-Cemented Strecker Stent The Strecker stent that is described in Example 26a is fixed in an electrolysis cell (FIG. 1), and a solution of phosphate buffer (0.1 mol/l, pH 5) is added. 100 mg of N,N-dimethyl-2-(3,3,5,11,13,13-hexamethyl-1,2-dithia-5,8, 11-triaza-cyclotridecan-8-yl)-ethylamine (produced according to WO 96/11918, Example 27) is added to the solution, and a voltage of 3.5 V is applied. Electrolysis is done for 15 minutes at room temperature. The stent is washed four times with water and can be used directly for labeling.

EXAMPLE 32b

Labeling with Re-186

The stent that is described in Example 32a is immersed in a solution that consists of 30 ml of acetate buffer (0.01 mol, pH 5 and 100 mg of tin(II)-chloride), and Re-186 solution (starting activity: 48.3 MBq) is added. It is stirred for 3 minutes at room temperature. The stent is washed twice with 3% aqueous sodium carbonate solution, then three times with physiological common salt solution. The stent showed a radioactivity of 1.44 MBq.

EXAMPLE 33

Labeling of a Gold-Cemented Stent with In-111 with In-situ Coupling of the Title Compound of Example 30a Using Electrochemical Reduction The Strecker stent that is described in Example 26a is fixed in an electrolysis cell (FIG. 1), and a solution of phosphate buffer (0.1 mol/l, pH 5) is added. 10 mg of the title compound of Example 30a, In-111 solution (starting activity: 34.6 MBq) is added to the solution, and a voltage of 3 V is applied. Electrolysis is done for 15 minutes at room temperature. The stent is washed twice with 3% aqueous sodium carbonate solution, twice with water and can be implanted directly. The stent showed a radioactivity of 0.77 MBq.

EXAMPLE 34

Labeling of a Gold-Cemented Stent with Cu-67 with In-situ Coupling of the Title Compound of Example 30a Electrochemical Reduction The Strecker stent that is described in Example 26a is fixed in an electrolysis cell (FIG. 1), and a solution of citric acid buffer (0.1 mol/l, pH 5) is added. 10 mg of the title compound of Example 30a, Cu-67 solution (starting activity: 36.7 MBq) is added to the solution, and a voltage of 1.8 V is applied. Electrolysis is done for 15 minutes at room temperature. The stent is washed twice with 3% aqueous sodium carbonate solution, of twice with water and can be implanted directly. The stent showed a radioactivity of 0.98 MBq.

EXAMPLE 35

Labeling with S-35

A stent that is produced according to 26a is put into a solution that consists of 5% aqueous hydrochloric acid, and a solution of S-35-cysteine (initial activity 37.5 MBq) is added. It is stirred for 5 minutes at room temperature. The stent is washed four times with physiological common salt solution. A radioactivity of 1.35 MBq is measured.

EXAMPLE 36

Labeling of a Strecker Stent with Cu-67

A Strecker stent (93 mg) is fixed in an electrolysis cell as described in FIG. 1. Then, the cell is made up with a 5% aqueous hydrochloric acid solution, and a Cu-67 solution is added (starting activity 47.4 MBq). Then, a voltage of 2 V is applied. Electrolysis is done for 5 minutes at room temperature. The radioactive solution is drained off via a valve, and the stent is washed four times with physiological common salt solution. A Strecker stent whose surface is labeled in this way contains a radioactivity of 1.56 MBq and can be used directly as an implant.

EXAMPLE 37

Labeling of a Nitinol Stent with Cu-67

A nitinol stent (about 500 mg) was labeled analogously as described in Example 1. Electrolysis is done for 10 minutes at 1.5 V, however. The stent showed a radioactivity of 3.21 MBq.

EXAMPLE 38

Labeling of a Nitinol Stent with Re-186

A nitinol stent (about 1000 mg) is fixed in an electrolysis cell as described in FIG. 1. Then, phosphate buffer (0.01 mol/l, pH 5) is added. Then, an Re-186 solution (starting activity 51.4 MBq) is added, and a voltage of 2.5 V is applied. Electrolysis is done for 10 minutes at room temperature. The radioactive solution is removed, and the stent is washed four times with physiological common salt solution. The stent showed a radioactivity of 2.44 MBq.

EXAMPLE 39

Labeling of a Palmaz-Schatz Stent (316 Stainless Steel) with Re-186

A Palmaz stent (about 200 mg) is fixed in an electrolysis cell (FIG. 1), and a solution that consists of 5% aqueous nitric acid, in which 150 mg of sodium chloride/ml is dissolved, is added. An Re-186 solution (starting activity: 37.4 MBq) is added, and a voltage of 2.3 V is applied. Electrolysis is done for 5 minutes at room temperature. The radioactive solution is removed, and the stent is washed four times with physiological common salt solution. The stent showed a radioactivity of 1.98 MBq.

EXAMPLE 40

Labeling of a Strecker Stent with Au-199

A Strecker stent (about 150 mg) is in an electrolysis cell (FIG. 1), and a solution of 7.5% aqueous hydrochloric acid is added. Then, an Au-199 solution (starting activity: 45.2 Mbq) is added, and a voltage of 1.5 V is applied. Electrolysis is done for 5 minutes at room temperature. The radioactive solution is removed, and the stent is washed four times with physiological common salt solution. The stent showed a radioactivity of 2.13 MBq.

EXAMPLE 41

Labeling of Strecker Stents with Au-199

A Strecker stent (about 350 mg) is in an el ctrolysis cell (FIG. 1), and a solution that consists of 2.5% aqueous hydrochloric acid, in which 100 mg of tetramethylammonium chloride/ml is dissolved, is added. Then, an Au-199 solution (starting activity: 55.6 MBq) is added, and a voltage of 1.2 V is applied. Electrolysis is done for 4 minutes at room temperature. The radioactive solution is removed, and the stent is washed four times with physiological common salt solution. The stent showed a radioactivity of 1.81 MBq.

EXAMPLE 42

Labeling of a Z-Stent (304 Stainless Steel) with Au-199

A Z-stent (about 250 mg) is in an electrolysis cell (FIG. 1), and a solution of 2.5% aqueous nitric acid, in which 100 mg of tetramethylammonium chloride/ml is dissolved, is added. Then, an Au-199 solution (starting activity: 38.6 MBq) is added, and a voltage of 1.2 V is applied. Electrolysis is done for 3 minutes at room temperature. The radioactive solution is removed, and the stent is washed four times with physiological common salt solution. The stent showed a radioactivity of 1.13 MBq.

EXAMPLE 43

Labeling of a Z-Stent (304 Stainless Steel) with Ag-110

A Z-stent (about 250 mg) is in an electrolysis cell (FIG. 1), and a solution of 5% aqueous nitric acid, in which 100 mg of tetramethylammonium nitrate/ml is dissolved, is added. Then, an Ag-110 solution (starting activity: 56.8 MBq) is added, and a voltage of 1.5 V is applied. Electrolysis is done for 2 minutes at room temperature. The radioactive solution is removed, and the stent is washed four times with physiological common salt solution. The stent showed a radioactivity of 1.54 MBq.

EXAMPLE 44

Labeling of a Nitinol Stent (304 Stainless Steel) with Ag-110

A nitinol stent (about 1500 mg) is in an electrolysis cell (FIG. 1), and a solution that consists of 7.5% aqueous nitric acid, in which 150 mg of tetramethylammonium nitrate/ml is dissolved, is added. Then, an Ag-110 solution (starting activity: 39.4 MBq) is added, and a voltage of 1.4 V is applied. Electrolysis is done for 10 minutes at room temperature. The radioactive solution is removed, and the stent is washed four times with water and twice with physiological common salt solution. The stent showed a radioactivity of 1.78 MBq.

EXAMPLE 45

Labeling of a Nitinol Stent with In-111

A nitinol stent (about 1500 mg) is in an electrolysis cell (FIG. 1), and a solution of 5% aqueous citric acid, in which 150 mg of tetramethylammonium chloride/ml is dissolved, is added. Then, an In-111 solution (starting activity: 51.3 MBq) is added, and a voltage of 3.5 V is applied. Electrolysis is done for 7 minutes at room temperature. The radioactive solution is removed, and the stent is washed twice with water and twice with physiological common salt solution. The stent showed a radioactivity of 1.45 MBq.

EXAMPLE 46

Labeling of a Z-Stent with In-111

A Z-stent (about 500 mg) is in an electrolysis cell (FIG. 1), and a solution that consists of 5% aqueous citric acid, in which 150 mg of tetramethylammonium chloride/ml is dissolved, is added. Then, an In-111 solution (starting activity: 36.9 MBq) is added, and a voltage of 3.8 V is applied. Electrolysis is done for 12 minutes at room temperature. The radioactive solution is removed, and the stent is washed twice with water and twice with physiological common salt solution. The stent showed a radioactivity of 1.77 MBq.

EXAMPLE 47

Labeling of a Strecker Stent with Au-199

In a cementation vessel (FIG. 2b), a Strecker stent (about 93 mg) is mixed with an aqueous hydrochloric acid solution (pH 3). Au-199 chloride solution (starting activity: 32.6 MBq) is added, and it is stirred for 10 minutes at room temperature. The stent is washed four times with physiological common salt solution and can be used directly for implantation. The stent showed a radioactivity of 1.22 MBq.

EXAMPLE 48

Labeling of a Strecker Stent with Ag-110

In a cementation vessel (FIG. 2a), a Strecker stent (about 496 mg) is mixed with an aqueous nitric acid solution (pH 4). Ag-110 nitrate solution (starting activity: 37.6 MBq) is added, and it is stirred for 10 minutes at room temperature. The stent is washed four times with dilute nitric acid (pH 3) and twice with water, and it can be used directly for implantation. The stent showed a radioactivity of 1.02 MBq.

EXAMPLE 49

Labeling of a Z-Stent with Au-199

In a cementation vessel (FIG. 2a), a Z-stent (about 987 mg) is mixed with an aqueous hydrochloric acid solution (pH 3). Au-199 chloride solution (starting activity: 41.5 MBq) is added, and it is stirred for 10 minutes at room temperature. The stent is washed four times with physiological common salt solution and can be used directly for implantation. The stent showed a radioactivity of 1.13 MBq.

EXAMPLE 50

Labeling of a Nitinol Stent with Au-199

In a cementation vessel (FIG. 2b), a nitinol stent (about 488 mg) is mixed with an aqueous hydrochloric acid solution (pH 3). Au-199 chloride solution (starting activity: 39.7 MBq) is added, and it is stirred for 10 minutes at room temperature. The stent is washed four times with physiological common salt solution and can be used directly for implantation. The stent showed a radioactivity of 0.98 MBq.

EXAMPLE 51

Labeling of a Strecker Stent with Re-186

A Strecker stent is brought into an electrolysis cell (FIG. 1), and a solution of sulfuric acid zinc sulfate solution (50 mg/ml, pH 5) is added. After a zinc anode is introduced, electrolysis is done at a voltage of 1.5 V for 10 minutes. The galvanized stent is washed four times with water. In a cementation vessel (FIG. 2a), the above-described stent is mixed with an aqueous citric acid solution (pH 5). Re-186 solution (starting activity: 41.6 MBq) is added, and it is stirred for 10 minutes at room temperature. The stent is washed four times with physiological common salt solution and can be used directly for implantation. The stent showed a radioactivity of 1.31 MBq.

EXAMPLE 52

Labeling of a Z-Stent (304 Stainless Steel) with Re-186

A Strecker stent is brought into an electrolysis cell (FIG. 1), and a solution of hydrochloric acid tin(II) chloride solution (50 mg/ml, pH 5) is added. After a tin anode is introduced, electrolysis is done at a voltage of 3 V for 5 minutes. The stent that is thus tinned is washed four times with water. In a cementation vessel (FIG. 2a), the above-described stent is mixed with an aqueous citric acid solution (pH 5). Re-186 solution (starting activity: 37.7 MBq) is added, and it is stirred for 10 minutes at room temperature. The stent is washed four times with physiological common salt solution and can be used directly for implantation. The stent showed a radioactivity of 1.44 MBq.

EXAMPLE 53

Labeling of a Nitinol Stent with Cu-67

In a cementation vessel (FIG. 2b), a nitinol stent (about 488 mg) is mixed with an aqueous hydrochloric acid solution (pH 3). Cu-67 sulfate solution (starting activity: 24.6 MBq) is added, and it is stirred for 10 minutes at room temperature. The stent is washed four times with physiological common salt solution and can be used directly for implantation. The stent showed a radioactivity of 1.55 MBq.

EXAMPLE 54

Labeling of a Palmaz Stent (316 Stainless Steel) with Cu-67

In a cementation vessel (FIG. 2a), a Palmaz stent (about 977 mg) is mixed with an aqueous hydrochloric acid solution (pH 3). Cu-67 sulfate solution (starting activity: 24.6 MBq) is added, and it is stirred for 10 minutes at room temperature. The stent is washed four times with physiological common salt solution and can be used directly for implantation. The stent showed a radioactivity of 0.88 MBq.

EXAMPLE 55

Labeling of a Palmaz Stent (316 Stainless Steel) with Re-186

A Palmaz stent is brought into an electrolysis cell (FIG. 1), and a solution of hydrochloric acid tin(II) chloride solution (50 mg/ml, pH 5) is added. After a tin anode is introduced, electrolysis is done at a voltage of 3 V for 5 minutes. The thus tinned stent is washed four times with water. In a cementation vessel (FIG. 2b), the above-described stent is mixed with an aqueous citric acid solution (pH 5). Re-186 solution (starting activity: 34.5 MBq) is added, and it is stirred for 10 minutes at room temperature. The stent is washed four times with physiological common salt solution and can be used directly for implantation. The stent showed a radioactivity of 1.98 MBq.

EXAMPLE 56

Labeling of a Palmaz Stent (316 Stainless Steel) with Ag-110

In a cementation vessel (FIG. 2a), a Palmaz stent (about 977 mg) is mixed with an aqueous nitric acid solution (pH 4). Ag-110 sulfate solution (starting activity: 24.6 MBq) is added, and it is stirred for 10 minutes at room temperature. The stent is washed four times with water and can be used directly for implantation. The stent showed a radioactivity of 1.12 MBq.

EXAMPLE 57

A Palmaz stent (15 mm, 80.3 mg, Johnson and Johnson) is covered with a layer of 1.0 ml of labeling solution that consists of 173 µl of sodium perrhenate solution (164 MBq) and 827 µl of 1 N HCl. The reaction vessel is placed in an ultrasound bath (80% US power) for 60 minutes at 50° C. Then, the stent is removed, rinsed with distilled $H_2O$ and dried. The dried stent carries an activity of 36.2 MBq=0.45 MBq/mg of stent. To remove non-specifically-bonded activity, the stent is incubated for 60 minutes in 1 ml of 0.9% NaCl solution at 37° C. After drying, the stent still carries an activity of 9.7 MBq=0.12 MBq/mg of stent.

EXAMPLE 58

A Palmatz stent (1/11 stent=26.2 mg, Johnson & Johnson) is covered with a layer of 1.5 ml of labeling solution that consists of 60 µl of perrhenate solution (60 MBq) and 1440 µl of 1 N HCl. The reaction vessel is tightly sealed and heated for 30 minutes to 100° C. (boiling water bath). Then, the stent is removed, rinsed with distilled $H_2O$ and dried. The dried stent carries an activity of 25.9 MBq (0.98 MBq/mg of stent). To remove or fix non-specifically-bonded activity, the stent is incubated for 10 minutes in 2 ml of 0.1 M gentisic acid/0.1 M $SnCl_2$ solution while being shaken. After drying, the stent carries an activity of 16.1 MBq (0.61 MBq/mg of stent).

EXAMPLE 59

A Palmatz stent (31.4 mg, Johnson & Johnson) is covered with a layer of 1.5 ml of labeling solution that consists of 60 µl of sodium perrhenate solution (81 MBq) and 1440 µl of 0.75 N HCl. The reaction vessel is tightly sealed and heated for 30 minutes to 100° C. (boiling water bath). Then, the stent is removed, rinsed with distilled $H_2O$ and dried. 27.1 MBq (0.86 MBq/mg of stent) is fixed on the dried stent. To remove non-specifically-bonded activity, the stent is then incubated in 2 ml of 0.1 M alcoholic tetrabutylammonium bromide solution for 10 minutes while being shaken. After drying, 17.0 MBq (0.54 MBq/mg of stent) is fixed on the stent.

EXAMPLE 60

After drying at room temperature several times, the stent of EXAMPLE 59 is immersed in a solution that consists of 16% vinyl acetate-acrylate polymer in ethyl acetate. After drying, the stent is ready for use.

| | Legend |
|---|---|
| 1 | Cover |
| 2 | Septum |
| 3 | Septum |
| 4 | Cell (Teflon or glass) |
| 5 | Stent |
| 6 | Solution |
| 7 | (+) Pt-anode, ring anode |
| 8 | Magnetic stirring rod |
| 9 | (−) Pt-cathode |

-continued

| | Legend |
|---|---|
| 10 | Shutoff valve |
| 11 | 2-Way Valve |
| 12 | Magnetic stirrer |
| 13 | Rinsing liquid |
| 14 | Active solution |

Addition of solutions: Hypodermic syringes or metering pumps When addition is done with hypodermic syringes: Put septa in the cover.

If electrolysis is carried out at an elevated temperature, the solution is preheated.

What is claimed is:

1. A process for preparing a radioactive stent comprising reacting a radioactive isotope with an adhesive that is a peptide, a fat or gold, said gold used in combination with a thiol-group-containing complexing agent, at 0–100° C., followed by coating the stent with the radiolabeled adhesive at 0° C.–100° C.

2. A process according to claim 1, wherein the radioactive isotope is one or more of Ag, Au, Ba, Bi, C, Co, Cr, Cu, Fe, Gd, Hg, Ho, In, Ir, Lu, Mn, Ni, P, Pb, Pd, Pm, Pt, Re, Rh, Ru, S, Sb, Sc, Sm, Tb, Tc or Y.

3. A process according to claim 1, wherein the adhesive is a peptide, or a fat.

4. A process according to claim 1, wherein the adhesive is gold in combination with a thiol-group-containing complexing agent.

5. A process according to claim 1, wherein the adhesive is a complexing peptide, or a complexing fat.

6. A process for preparing a radioactive stent comprising coating a non-radioactive stent with an adhesive that is a peptide, a fat or gold, said gold used in combination with a thiol-group-containing complexing agent at 0° C.–100° C., followed by coating the stent with a radioactive isotope by placing the stent at 0–100° C. into a solution of the radioactive isotope.

7. A process according to claim 6, wherein the radioactive isotope is one or more of Ag, Au, Ba, Bi, C, Co, Cr, Cu, Fe, Gd, Hg, Ho, In, Ir, Lu, Mn, Ni, P, Pb, Pd, Pm, Pt, Re, Rh, Ru, S, Sb, Sc, Sm, Tb, Tc or Y.

8. A process according to claim 6, wherein the adhesive is a peptide, or a fat.

9. A process according to claim 6, wherein the adhesive is gold in combination with a thiol-group-containing complexing agent.

10. A process according to claim 6, wherein the adhesive is a complexing peptide, or a complexing fat.

\* \* \* \* \*